(12) United States Patent
Galliher et al.

(10) Patent No.: US 9,080,983 B2
(45) Date of Patent: Jul. 14, 2015

(54) SPLIT SENSOR AND HOUSING ASSEMBLY FOR FLEXIBLE WALL

(71) Applicant: XCELLEREX, INC., Marlborough, MA (US)

(72) Inventors: Parrish M. Galliher, Littleton, MA (US); Thomas Erdenberger, Arlington, MA (US); Colin R. Tuohey, Medway, MA (US); Richard L. Damren, Marlborough, MA (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 58 days.

(21) Appl. No.: 13/751,587

(22) Filed: Jan. 28, 2013

(65) Prior Publication Data

US 2013/0196361 A1    Aug. 1, 2013

Related U.S. Application Data

(60) Provisional application No. 61/591,060, filed on Jan. 26, 2012.

(51) Int. Cl.
*G01N 21/00* (2006.01)
*G01N 21/76* (2006.01)
*G01N 21/05* (2006.01)
*G01N 21/84* (2006.01)
*G01N 21/25* (2006.01)
*G01N 21/27* (2006.01)

(52) U.S. Cl.
CPC .............. *G01N 21/76* (2013.01); *G01N 21/251* (2013.01); *G01N 21/276* (2013.01); *G01N 21/8483* (2013.01); *G01N 2021/052* (2013.01)

(58) Field of Classification Search
CPC ........................... G01N 21/8483; G01N 21/76
USPC ....................................................... 422/82.05
See application file for complete search history.

(56) References Cited

U.S. PATENT DOCUMENTS 6,492,808 B1 * 12/2002 Sukhorukov et al. ......... 324/242

* cited by examiner

*Primary Examiner* — Jill Warden
*Assistant Examiner* — Brittany Fisher
(74) *Attorney, Agent, or Firm* — Ziegler IP Law Group, LLC

(57) ABSTRACT

Disclosed is a sensor and housing assembly for a single-use bioreactor system, including a device for operatively associating a sensor with a flexible wall, the device comprising an internal housing portion that is removable and variably positionable on an internal surface of the flexible wall, the internal housing portion comprising a chemical detector sensor, which may be an optical chemical detector sensor.

8 Claims, 4 Drawing Sheets

SPLIT SENSOR AND HOUSING ASSEMBLY FOR FLEXIBLE WALL

RELATED APPLICATIONS

This application claims the priority benefit of U.S. Provisional Application Nos. 61/591,060 filed on Jan. 26, 2012, the teachings of which are incorporated herein by reference in their entirety.

FIELD OF INVENTION

This disclosure relates generally to biochemical processing systems and methods, and in particular, to optical sensor technology.

BACKGROUND

In general, optical chemical sensing technology includes the use of an optical excitation source such as light to excite an optical chemical sensor. In response to the excitation, the optical chemical sensor emits luminescence or absorbs light which is measured by a detector. If the optical chemical sensor is in fluidic contact with the liquid media in a cell culture, the pH of the liquid media or the dissolved oxygen (DO) in the liquid media can be determined by analysis of the luminescence emitted from the sensor or of the amount of light absorbed by the sensor. Changes in either the luminescence emitted, or in the amount of light absorbed can be used to monitor in real time changes in pH or changes in the concentration of an analyte.

The use of optical chemical sensors in bioprocessing provides a means for automating the monitoring, adjusting, and optimizing of conditions within a bioreactor, thereby accelerating pharmaceutical manufacturing processes, such as, e.g., processes that include growing cells for production of therapeutic proteins, monoclonal antibodies, vaccines, and the like.

Biological, chemical, and/or pharmaceutical manufacturing processes traditionally have been carried out in stainless steel or glass vessels. Increasingly, however, single-use or flexible-walled bags and tubing systems have been used for bioprocessing.

As is well known by those of skill in the art, many problems are encountered in process of attaching various types of sensor assemblies to polymeric or flexible plastic materials, or in securing a sensor assembly to a film, flexible bags, and flexible tubing, A conventional optical sensor and its housings for flexible or semi-rigid containers (such as disposable bags or plastic tubing) require an attachment such as a "window" or a "receiver" that is attached to the flexible wall of the container. One disadvantage of this commercially available design is that it requires an additional assembly and components to attach the sensor-housing assembly to the flexible wall or semi-rigid wall. Another disadvantage of current designs is that the design also requires a penetration through the wall of the flexible container or tubing in which the "window" or sensor and its housing "receiver" is attached. The penetration can lead to leakage of liquids in the container or tubing or contamination of the liquids. Contamination or potential contamination is an ongoing problem of critical concern in pharmaceutical or medical applications. Another disadvantage of currently available optical sensor assemblies for use in flexible wall systems is that, following the attachment of the sensor and its housing to a flexible bag or tubing, the position of the sensor and its housing assembly cannot be moved.

SUMMARY OF THE INVENTION

Disclosed herein are a method and a device for operatively associating at least one optical chemical sensor with a flexible wall in a chemical, pharmaceutical or biological reactor system, the method and device overcoming some of the aforementioned problems. The disclosed device can be used with a single-use bioreactor, mixer, or tubing having at least one flexible wall or a flexible portion of a wall.

In one aspect, the invention includes a sensor and a housing assembly that may be associated with a flexible wall container or tubing, and comprises two separate sensors positioned on either side of the wall of the flexible container or tubing. One advantage of the disclosed system is that it requires a reduced number of components and steps to attach the sensor and its housing to the flexible wall. A second advantage of the disclosed system is that the assembly does not require a penetration through the wall of the flexible container. A third advantage is that the sensor and its housing assembly is not fixed to the wall permanently and can therefore be moved or repositioned at will.

In one embodiment, the sensor assembly includes an internal detector sensor and its housing positioned on an internal surface of the wall of a flexible bag or tubing, and an external activator and/or reader sensor and its housing positioned on an external surface of the wall of a flexible bag or tubing or on a support structure for the flexible bag or tubing.

Disclosed herein is a sensor and housing assembly 100 for a single-use bioreactor system, comprising a device for operatively associating a sensor with a flexible wall, the device comprising: an internal housing portion 130 removable and variably positionable on an internal surface of the flexible wall 112, the internal housing portion 130 comprising: an internal portion of a chemical detector sensor sealably embedded in a detector sensor housing 132, and at least one portion of an internal magnetic material 136, 138 positioned within the internal housing portion 130 for variably positioning and removing the internal housing portion 130 on the internal surface of the flexible wall 112; and an external housing portion 140 positioned on an external surface of a support structure 110 adjacent to the external surface of the flexible wall 114, the external housing portion 140 comprising: an external portion of an activator sensor sealably embedded in an activator sensor housing 142; and at least one portion of an external magnetic material 146, 148 positioned within the external housing portion 140 or adjacent thereto for holding the detector sensor 132 proximate and aligned to activator sensor 142, and for variably positioning the internal housing portion 130 on the internal surface of the flexible wall 112 by magnetic interaction between the at least one portion of the external magnetic material 146, 148 and the at least one portion of the internal magnetic material 136, 138 within the internal housing portion 130.

Another embodiment of the invention is a sensor and housing assembly 400 for a single-use bioreactor system, comprising a device for operatively associating a sensor with a flexible wall, the device comprising: an internal housing portion 430 removable and variably positionable on an internal surface of the flexible wall 412, the internal housing portion 430 comprising: an internal portion of a chemical detector sensor sealably embedded in a detector sensor housing 432, and at least one portion of an internal magnetic material 436, 438, positioned within the internal housing portion 430 for variably positioning and removing the internal housing portion 430 on the internal surface of the flexible wall 412; and an external housing portion 440 positioned on the external surface of the flexible wall 414, the external housing portion 440 comprising: an external portion of an activator sensor sealably embedded in an activator sensor housing 442; and at least one portion of an external magnetic material 446, 448, positioned within the external housing portion 440 or adjacent thereto for holding the detector sensor 432 proximate and aligned to the activator sensor 442, and for variably positioning the internal housing portion 430 on the internal surface of the flexible wall 412 by magnetic interaction between the at least one portion of the external magnetic material 446, 448, and the at least one portion of the internal magnetic material 436, 438 within the internal housing portion 430.

Another embodiment of the invention is a sensor and housing assembly 200 for a single-use, collapsible bioprocessing bag comprising at least two oppositely-positioned internal flexible wall portions 216, 212, the sensor and housing assembly 200 comprising: an internal housing portion 230 attached to one end of a strut 260 having an opposite end attached to the internal flexible wall portion 216, the internal housing portion 230 comprising an internal portion of a chemical detector sensor sealably embedded in a chemical detector sensor housing 232, the strut 260 spanning the interior of the single-use bioprocessing bag and biasing the internal housing portion 230 and chemical detector sensor housing 232 against the internal flexible wall portion 212; and an external housing portion 240 attached on one side thereof to the external surface 210 of a collapsible bioprocessing bag support structure, the opposite side of the external housing portion 240 lying adjacent to or biased against the external flexible wall portion 214, and wherein the external housing portion 240 comprises: an external portion of an activator sensor sealably embedded in an activator sensor housing 242; the activator sensor housing 242 positioned proximate and aligned to the detector sensor housing 232.

BRIEF DESCRIPTION OF THE DRAWINGS

The foregoing and other non-limiting objects, features and advantages of the invention will be apparent from the following more particular description of illustrative embodiments of the invention, as illustrated in the accompanying drawings in which like reference characters refer to the same parts throughout the different views. The drawings are schematic and not intended to be drawn to scale, emphasis instead being placed upon illustrating the principles of the invention. The drawings are schematic and not intended to be drawn to scale, emphasis instead being placed upon illustrating the principles of the invention. The features illustrated or described in connection with one exemplary embodiment can be combined with the features of other embodiments. Such modifications and variations are intended to be included within the scope of the present invention.

DETAILED DESCRIPTION

Figure 1:
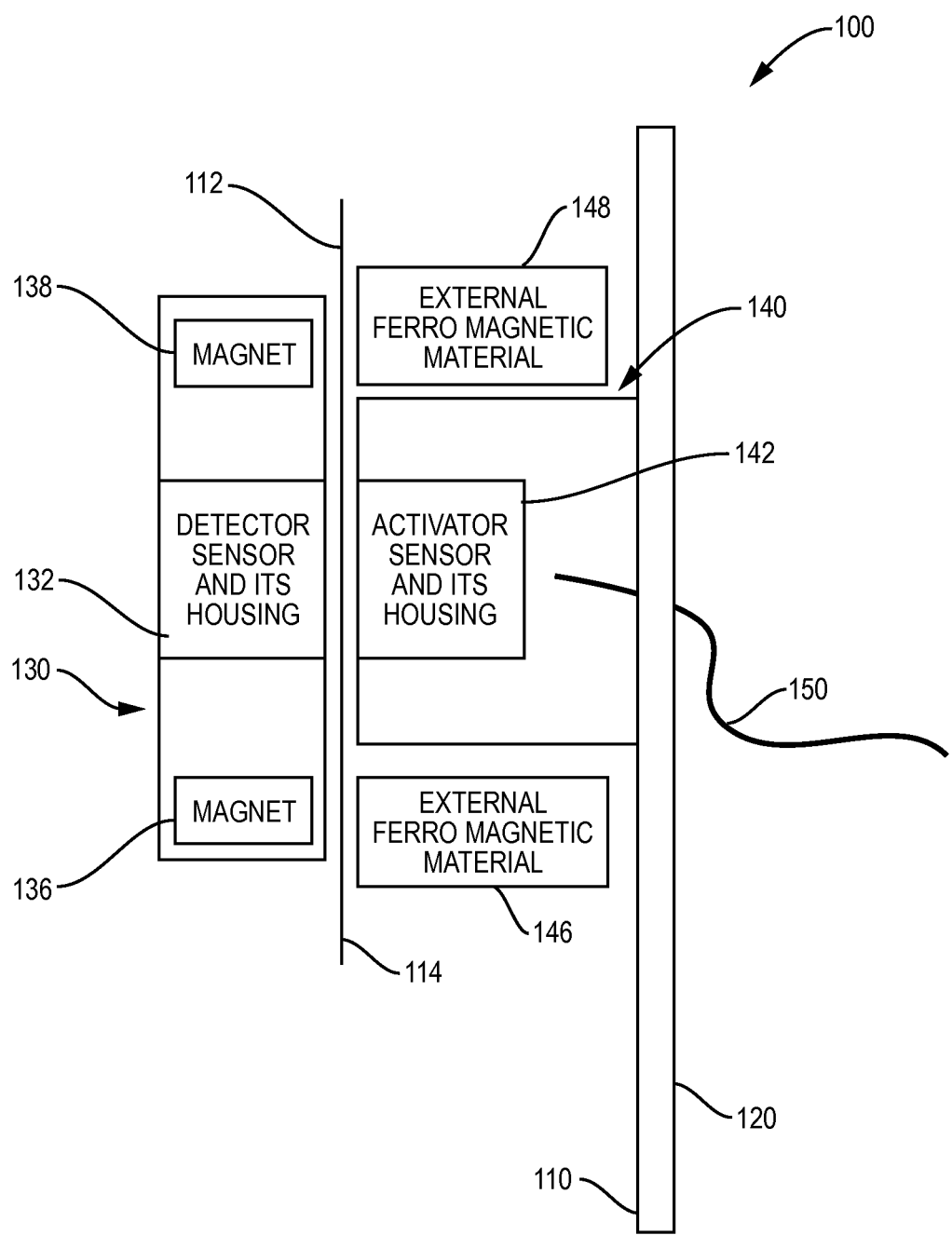
FIG. 1 is a schematic representation of a sensor and housing assembly according to an embodiment of the invention, showing a detector sensor and its housing associated with internal magnetic material and variably positionable on the inside of a flexible wall, the detector sensor held by magnetic attraction to an external activation sensor associated with external magnetic material.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "e.g.," and "in one embodiment."

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but can include other elements not expressly listed or inherent to such process, article, or apparatus. Further, unless expressly stated to the contrary, "or" refers to an inclusive or and not to an exclusive "or."

Disclosed herein is a sensor and housing assembly for use in a single-use bioprocessing system, the sensor and housing assembly comprising a device for operatively associating a sensor with a flexible wall such that the detector sensor is removable and variably positionable on an internal surface of the flexible wall. The device is configured to hold the detector sensor proximate and aligned to an activation sensor. The disclosed system will be referred to herein as two sensors: a detector sensor and an activator or reader sensor. The system could also be considered as a split sensor that includes a detector sensor and an activator or reader sensor. Non-limiting examples of the disclosed system are polymeric, optical, UV, inductive, conductive, heat, acoustic, RFID and electrochemical sensors. The disclosed sensor and housing assembly may be associated with a flexible wall container or tubing, and comprise two separate sections positioned on either side of the wall of the flexible container or tubing.

One advantage of the disclosed system is that it requires a reduced number of components and steps to attach the sensor and its housing to the flexible wall. A second advantage of the disclosed system is that the assembly does not require a penetration through the wall of the flexible container. A third advantage is that the sensor and its housing assembly is not fixed to the wall permanently and can therefore be moved or repositioned at will.

In one embodiment, the sensor assembly includes an internal detector sensor and its internal housing positioned on an internal surface of the wall of a flexible bag or tubing, and an external activator sensor and its external housing positioned on an external surface of the wall of a flexible bag or tubing.

In one embodiment of the invention, the internal sensor may comprise a detector and emitter, and an external sensor may comprise an activator and/or a reader, with a communication wire or lead arranged to send a signal to a control device or computer.

In one embodiment of the invention, an external sensor serves to activate the internal detector and emitter optical sensor directly through the flexible wall of the container or tubing. The internal optical sensor and its housing contains a detection device that performs the function of detecting the analyte present inside the flexible walled container. Non-limiting examples of the analyte or target measurement are dissolved oxygen, pH, metabolites, sugars, soluble molecules, gases, particles, and the like.

In another embodiment of the invention, both the detector and emitter and the activator and/or the reader are on the inside; and the light source is on the outside, positioned to shine through the bag or tubing wall.

Turning now to the figures, FIG. 1 schematically shows a sensor and a housing assembly according to an embodiment of the invention. FIG. 1 depicts a sensor and housing assembly 100 for a single-use bioreactor system, comprising a device for operatively associating a sensor with a flexible wall, the device comprising: an internal housing portion 130 removable and variably positionable on an internal surface of the flexible wall 112, the internal housing portion 130 comprising: an internal portion of a chemical detector sensor sealably embedded in a detector sensor housing 132, and at least one portion of an internal magnetic material 136, 138 positioned within the internal housing portion 130 for variably positioning and removing the internal housing portion 130 on the internal surface of the flexible wall 112; and an external housing portion 140 positioned on an external surface of a support structure 110 adjacent to the external surface of the flexible wall 114, the external housing portion 140 comprising: an external portion of an activator sensor sealably embedded in an activator sensor housing 142; and at least one portion of an external magnetic material 146, 148 positioned within the external housing portion 140 or adjacent thereto for holding the detector sensor 132 proximate and aligned to activator sensor 142, and for variably positioning the internal housing portion 130 on the internal surface of the flexible wall 112 by magnetic interaction between the at least one portion of the external magnetic material 146, 148 and the at least one portion of the internal magnetic material 136, 138 within the internal housing portion 130.

In the embodiment shown in FIG. 1, the internal magnetic material 136, 138 is attracted to the external magnetic material 446, 448 positioned within the external housing portion 440 or adjacent thereto. The magnetic interactions assist in positioning or appropriately aligning the internal detector sensor opposite the external activator sensor so that the detector sensor can be activated by signals such as light emitted or absorbed by the activator sensor through the flexible wall of the container, a portion of which flexible wall may be transparent or translucent.

In one embodiment of a method for using the disclosed system, the activator sensor may produce light of a particular wavelength which excites or activates an optical chemical sensor which in turn emits light or absorbs light, which light emission or absorption is measured by the detector sensor. The quantity of light absorbed or emitted by the optical chemical sensor is correlated with the concentration of an analyte, e.g., oxygen, or with the pH of the media in the flexible container.

FIG. 1 also shows a communication wire or lead 150 for the activator sensor and its housing leading from the external housing portion 140 and passing through the support structure from the internal surface to the external surface thereof. The communication wire or lead 150 is arranged to send a signal to a control device or computer.

In one embodiment of the invention, an external portion of the sensor and its housing serves to activate the inside detector and emitter portion of the optical sensor and its housing directly through the wall of the flexible container. The inside portion of the optical sensor and its housing contains a detection device that performs the function of detecting the analyte present inside the flexible wall container.

In one embodiment of the invention, at least one of the internal magnetic material and the external magnetic material comprises a ferro-magnetic material.

In another embodiment, the external housing portion 140 is removable and variably positionable on the external surface of the support structure 110. The support structure 110 may include a steel vessel surrounding an supporting a flexible, collapsible bag during use.

In one embodiment of the invention the sensor is an optical chemical sensor. The optical chemical sensor may be an oxygen sensor or a pH sensor.

The disclosed invention also relates to a method of using a disclosed sensor and housing assembly, wherein at least two removable and variably positionable optical chemical detector sensors are used during bioprocessing to measure at least two different cell culture conditions.

Figure 4:
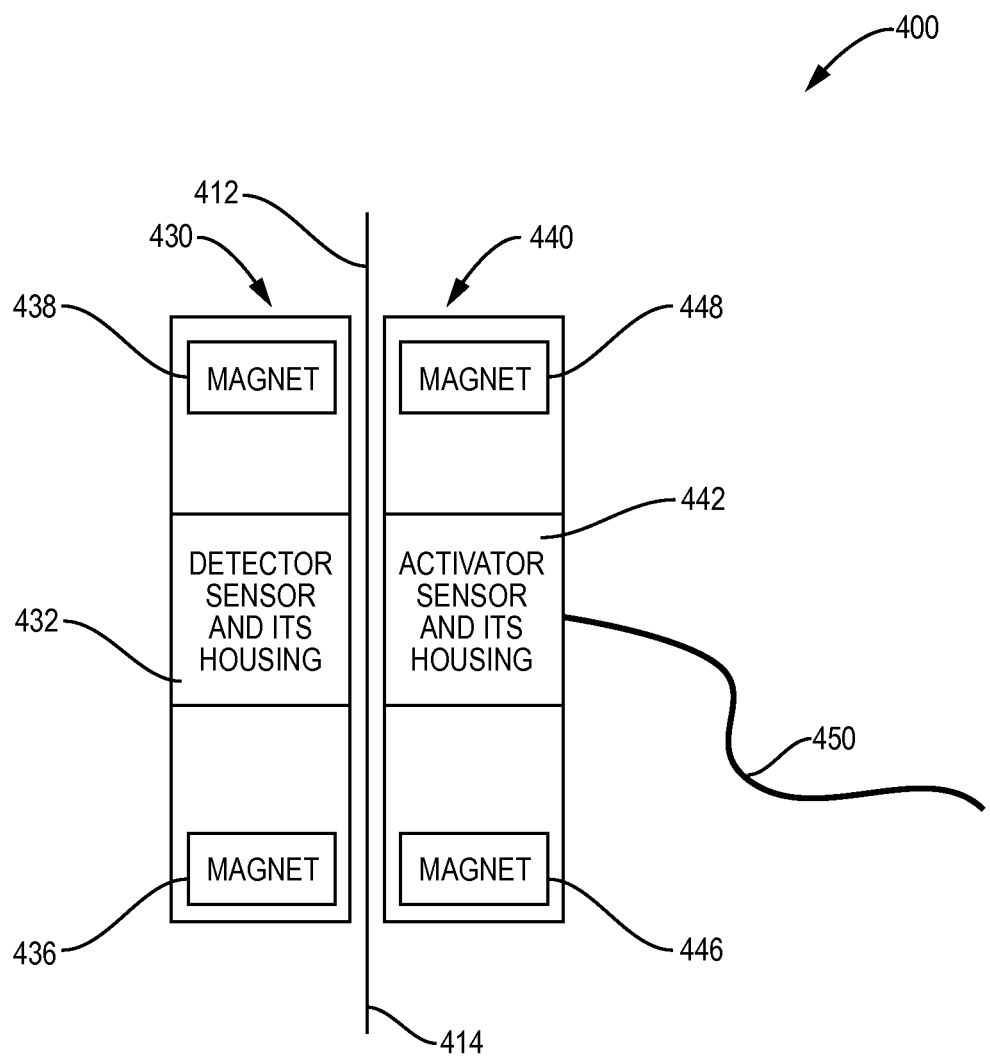
FIG. 4 is a schematic representation of a sensor and housing assembly according to another embodiment of the invention, wherein the detector sensor and the activation sensor are held in alignment with one another on opposite sides of the flexible wall through magnetic attraction, but are variably positionable on the flexible wall.

Another embodiment of the invention is depicted in FIG. 4, wherein an external activator sensor housing is aligned with the internal detector sensor and held to the external wall 414. FIG. 4 shows a sensor and housing assembly 400 for a single-use bioreactor system, comprising a device for operatively associating a sensor with a flexible wall, the device comprising: an internal housing portion 430 removable and variably positionable on an internal surface of the flexible wall 412, the internal housing portion 430 comprising: an internal portion of a chemical detector sensor sealably embedded in a detector sensor housing 432, and at least one portion of an internal magnetic material 436, 438, positioned within the internal housing portion 430 for variably positioning and removing the internal housing portion 430 on the internal surface of the flexible wall 412; and an external housing portion 440 positioned on the external surface of the flexible wall 414, the external housing portion 440 comprising: an external portion of an activator sensor sealably embedded in an activator sensor housing 442; and at least one portion of an external magnetic material 446, 448, positioned within the external housing portion 440 or adjacent thereto for holding the detector sensor 432 proximate and aligned to the activator sensor 442, and for variably positioning the internal housing portion 430 on the internal surface of the flexible wall 412 by magnetic interaction between the at least one portion of the external magnetic material 446, 448, and the at least one portion of the internal magnetic material 436, 438 within the internal housing portion 430.

Figure 2:
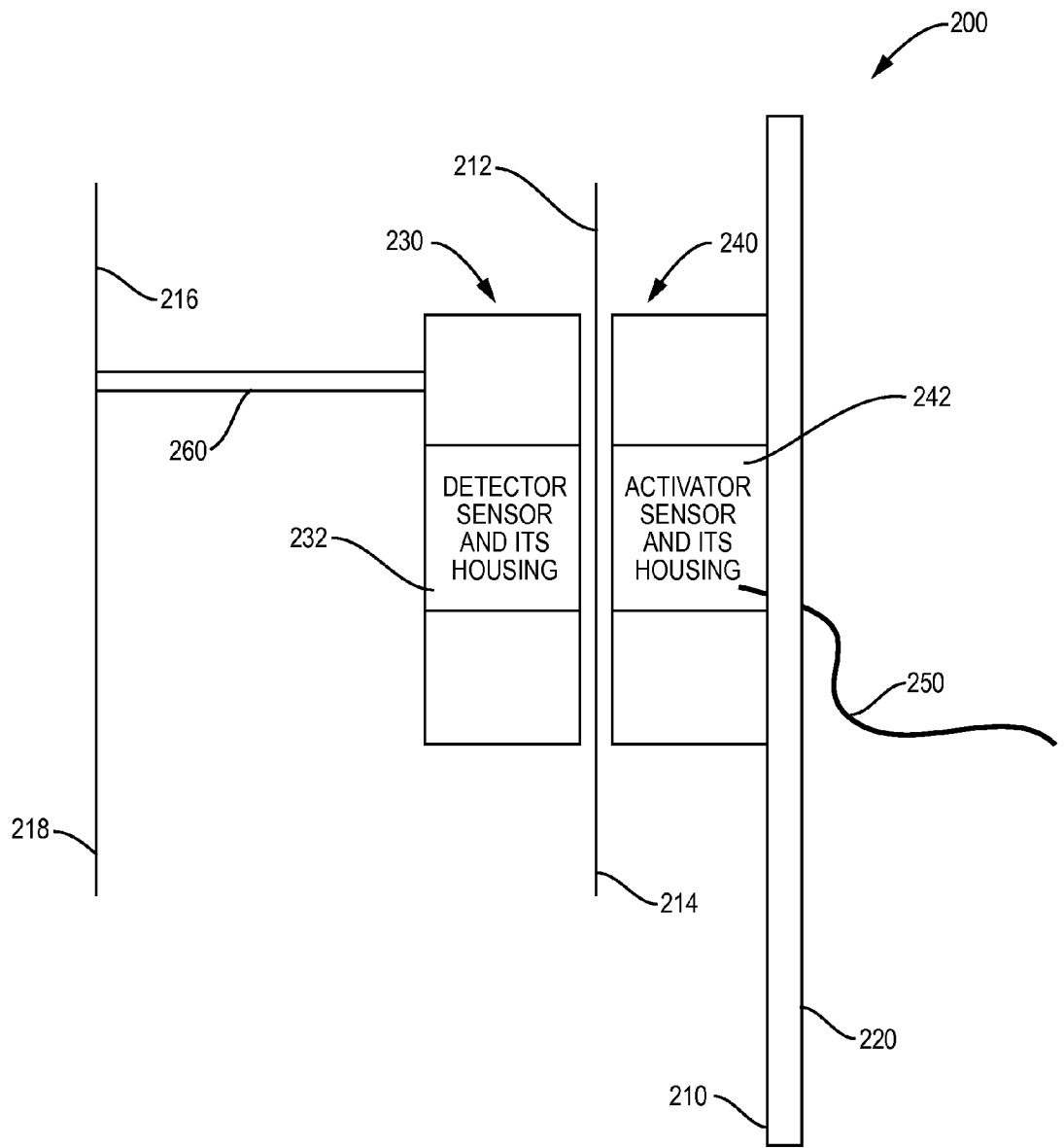
FIG. 2 is a schematic representation of a sensor and housing assembly according to another embodiment of the invention, wherein the chemical detector sensor and its housing are attached to a strut within a flexible bioprocessing bag and biased against a wall of the bag and against an activator sensor attached to a bag support.

Also disclosed and schematically shown in FIG. 2 is an embodiment wherein the external activator sensor and its housing 242 is attached to the inside wall 210 of the support structure and pressed between the external support structure supporting the flexible container and the external surface of the flexible wall 214. The communication wire or lead 250 for the activator sensor and its housing is shown leading from the external housing portion 240 and passing through the support structure from the internal surface 210 to the external surface 220 thereof. The communication wire or lead 150 is arranged to send a signal to a control device or computer.

The sensor and housing assembly 200 shown in FIG. 2 for a single-use, collapsible bioprocessing bag comprising at least two oppositely-positioned internal flexible wall portions 216, 212, the sensor and housing assembly 200 comprising: an internal housing portion 230 attached to one end of a strut 260 having an opposite end attached to the internal flexible wall portion 216, the internal housing portion 230 comprising an internal portion of a chemical detector sensor sealably embedded in a chemical detector sensor housing 232, the strut 260 spanning the interior of the single-use bioprocessing bag and biasing the internal housing portion 230 and chemical detector sensor housing 232 against the internal flexible wall portion 212; and an external housing portion 240 having one side attached to external surface 210 of a collapsible bioprocessing bag support structure, and an opposite side of the external housing portion 240 lying adjacent to or biased against the external flexible wall portion 214, and wherein the external housing portion 240 comprises: an external portion of an activator sensor sealably embedded in an activator sensor housing 242; the activator sensor housing 242 positioned proximate and aligned to the detector sensor housing 232.

Figure 3:
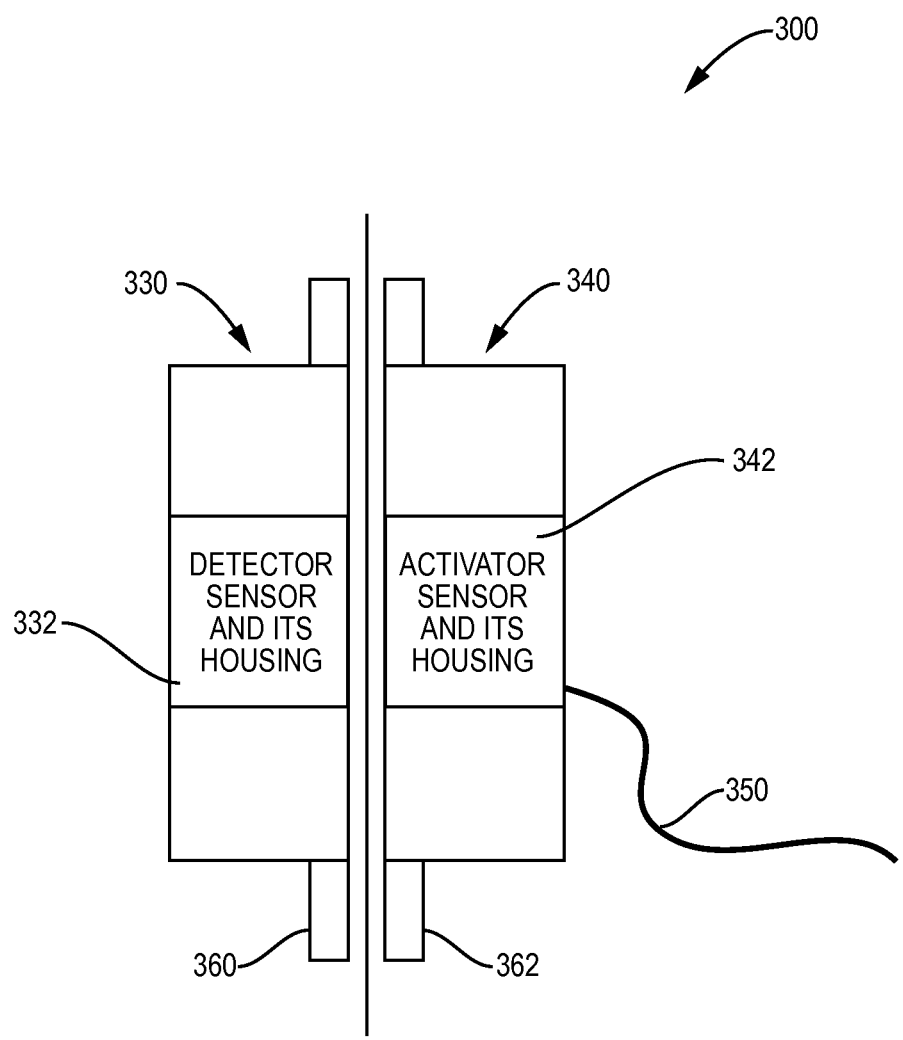
FIG. 3 is a schematic representation of a sensor and housing assembly according to another embodiment of the invention, wherein the chemical detector sensor and its housing are attached to an internal surface of a flexible wall of a container and aligned with an external activation sensor attached to an external surface of the flexible wall.

FIG. 3 shows another embodiment of the inventive sensor assembly 300 wherein an external housing portion 340 having a flange and comprising an external activator sensor 342 is attached by means of the flange 362 to the external side of flexible wall of a container or tubing, the flexible wall shown as a vertical line between external housing portion 340 and internal housing portion 330. Flange 362 can be welded, fused, or embedded to or in the external surface of the flexible wall. In this embodiment, the internal housing portion 330 includes a detector sensor and its housing 332 aligned with the external activator sensor 342. The internal housing portion 330 includes a flange, 360 that can be welded or fused to the internal surface of the flexible wall of the bioreactor, mixer, or tubing.

Although much of the description herein involves exemplary applications of the present invention related to single-use bioreactor bags, mixer bags, and flexible tubing systems, the invention and its uses are not so limited, and it should be understood that aspects of the invention can also be used in other settings, including those involving containment systems in general, as well as systems for containment or for mixing or other processing.

The terms "rigid" and "semi-rigid" are used herein interchangeably to describe structures that are "non-collapsible," that is to say structures that do not fold, collapse, or otherwise deform under normal forces to substantially reduce their elongate dimension. Depending on the content "semi-rigid" can also denote a structure that is more flexible than a "rigid" element, e.g., a bendable tube or conduit, but still one that does not collapse longitudinally under normal conditions and forces. "Flexible container", "flexible bag", or "collapsible bag" as used herein, indicates that the container or bag is unable to maintain its shape and/or structural integrity when subjected to the internal pressures, for example, pressures resulting from the weight or hydrostatic pressure of liquids or gases contained therein without the benefit of a separate support structure. A reusable support structure such as a rigid vessel or tank can be utilized to surround and support the collapsible bag.

The term "vessel" as used herein generally refers to a support structure or tank surrounding and supporting a flexible bag. The term vessel is intended to encompass bioreactor vessels as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. In the bioprocessing industry, the term "vessel" is often used to define any enclosed bioprocessing volume in which the regulation of temperature is desirable. The terms "reactor" and "reactor system" are used interchangeably herein and are intended to encompass chemical, pharmaceutical and biological reactors, including but not limited to cell culturing and vaccine producing reactors, as known in the art.

A support structure that can be used to support a collapsible bag can have any suitable shape able to surround and/or contain the bag. In some cases, the support structure is reusable. The support structure can be formed of a substantially rigid material. Non-limiting examples of materials that can be used to form the support structure include stainless steel, aluminum, glass, resin-impregnated fiberglass or carbon fiber, polymers such as high-density polyethylene, polyacrylate, polycarbonate, polystyrene, nylon or other polyamides, polyesters, phenolic polymers, and combinations thereof. The materials can be certified for use in the environment in which it is used. For example, non-shedding materials can be used in environments where minimal particulate generation is required. In addition, the support structure can include other components, such as channels, for flowing a fluid and/or containing a material to modify the properties of the support structure.

A reusable support structure or vessel can have any suitable volume and, in some instances, has a volume substantially similar to that of the container contained in the support structure. The reusable support structure can have a volume between, for example, of from about 5 liters to about 5,000 liters. Volumes greater than 10,000 liters are also possible.

As described herein a vessel such as a collapsible bag can include a mixing system for mixing contents of the vessel. In some cases, more than one agitator or impeller can be used to increase mixing power, and the impellers can be the same or different. A mixing system of a vessel can be disposable or intended for a single use, along with the container in some cases. Various methods for mixing fluids can be implemented in the container. For instance, impellers based on magnetic actuation, sparging, and/or air-lift can be used. Direct shaft-drive mixers that are sealed and not magnetically coupled can also be used.

Many disclosed examples include the use of collapsible bags, liners, or flexible containers. In addition, an embodiment of the invention can include systems utilizing semi-flexible containers and other configurations involving liquid containment.

The collapsible bag can be made out of inherently flexible materials, such as many plastics, or can be made out of what are normally considered rigid materials such as glass or certain metals, but having a thickness or other physical properties rendering the container as a whole unable to maintain its shape or structural integrity when subjected to the internal pressures expected during operation without the benefit of a separate support structure. In some embodiments, collapsible bags include a combination of flexible materials and substantially rigid materials such as a rigid polymer, metal, or glass. For example, the collapsible bag, liner or other container can include rigid components such as connections, ports, supports for a mixing and/or antifoaming system.

In some embodiments, a rigid container or a collapsible bag comprises a polymeric material, for example, as a bulk material. Polymeric materials, such as the ones described herein, can be selected or formulated to have suitable physical and mechanical characteristics, for example, by tailoring the amounts of components of polymer blends to adjust the degree of any expected cross-linking. For instance, those of ordinary skill in the art can choose suitable polymers for use in containers based on factors such as the polymer's thermal conductivity, compatibility with certain processing techniques, compatibility with thermally-conductive materials, compatibility with any materials, such as cells, nutrients, solvents, contained in the container, and compatibility with sterilizations or other treatments or pre-treatments associated with performing a reaction inside the container.

In some embodiments, a collapsible bag is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. Portions of the flexible container can comprise a substantially rigid material such as a rigid polymer, for example, high density polyethylene, metal, or glass. Substantially rigid materials can be utilized in areas for supporting fittings, for example.

The container can have any suitable thickness for holding a liquid and can be designed to have a certain resistance to puncturing during operation or while being handled. The thickness of a material such as a container wall is often specified in "mils." A mil is a unit of length equal to one thousandth ($10^{-3}$) of an inch, which is equivalent to 0.0254 millimeter. The unit "millimeter" is abbreviated herein as "mm." For example, a thickness of the flexible wall portions of a collapsible bag suitable for use in an embodiment of the invention can be less than 10 mils (less than 0.254 mm), or from about 10 mils to about 100 mils (from about 0.254 mm to about 2.54 mm) or from about 15 mils to about 70 mils (from about 0.38 mm to about 1.78 mm), or from about 25 mils to about 50 mils (from about 0.64 mm to about 1.27 mm). In yet another example, the walls of a container can have a total thickness of about 250 mils.

Components that are integrated with collapsible bags or other containers can be formed in any suitable material, that may be the same or different from the material of the bag or container. In one embodiment, a container is formed in a first polymer and a component is formed in a second polymer that is different, for example, in composition, molecular weight, or chemical structure, from the first polymer. Those of ordinary skill in the art will be familiar with material processing techniques and will be able to use such techniques in the methods described herein to choose suitable materials and combinations of materials.

A rigid container or a collapsible bag suitable for use in an embodiment of the invention can have any size for containing a liquid. For example, the container can have a volume from about 0.1 liter to about 10,000 liters (from about 100 cubic centimeters to about $1\times10^7$ cubic centimeters.) The term "cubic centimeter" will be abbreviated herein as "$cm^3$." In other non-limiting examples, the container can have a volume from about 5 liters to about 5,000 liters (from about 5,000 $cm^3$ to about $5\times10^6$ $cm^3$), or from about 40 liters to about 1,000 liters (from about $4\times10^4$ $cm^3$ to about $1\times10^6$ $cm^3$). Volumes greater than 10,000 liters ($1\times10^7$ $cm^3$) are also possible. The suitable volumes can depend on the particular use of the container. For example, a collapsible bag used as a heat exchanger can have a smaller volume than a collapsible bag used to hold and store a large amount of fluid.

In general, as used herein, a component of an inventive system that is "operatively associated with" one or more other components indicates that such components are directly connected to each other, in direct physical contact with each other without being connected or attached to each other, or are not directly connected to each other or in contact with each other, but are interconnected mechanically, electrically, fluidically, or remotely via electromagnetic signals, so as to cause or enable the components so associated to perform their intended functionality.

It should be understood that not all of the features shown in the figures need be present in all embodiments of the invention and that the illustrated elements can be otherwise positioned or configured. Also, additional elements can be present in other embodiments, such as the elements described herein.

In some cases, sensors can be connected to a sensor electronics module (not shown), the output of which can be sent to a terminal board and/or a relay box. Various sensors for controlling and/or monitoring one or more process parameters inside the container such as, for example, temperature, pressure, pH, dissolved oxygen (DO), dissolved carbon dioxide ($DCO_2$), mixing rate, and gas flow rate, can be used. The results of the sensing operations can be input into a computer or computer-implemented control system for calculation and control of various parameters such as temperature and weight/volume measurements, and for display and user interface. Such a control system can also include a combination of electronic, mechanical, and/or pneumatic systems to control heat, air, or liquid delivered to or withdrawn from the container as required to stabilize or control the environmental parameters of the process operation.

A control system can control one or more operations of a single reactor for a biological or chemical reaction, or of multiple reactors that are separate or interconnected. In some embodiments, the contents inside the container do not contact the reusable support structure and, therefore, the reusable support structure can be reused after carrying out a particular chemical or biological reaction without being sterilized, while the container and/or fittings connected to the container can be discarded. In other embodiments, the container, fittings, and/or reusable support structure can be reused (for example, after cleaning and sterilization).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will readily appreciate that all parameters, dimensions, materials, and configurations described herein are meant to be exemplary and that the actual parameters, dimensions, materials, or configurations will depend upon the specific application for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention can be practiced otherwise than as specifically described and claimed. The present invention is directed to each individual feature, system, article, material, kit, and/or method described herein, and to any combination of the foregoing.

It should also be understood that, unless clearly indicated to the contrary, in any methods claimed herein that include more than one step or act, the order of the steps or acts of the method is not necessarily limited to the order in which the steps or acts of the method are recited.

Features groups described in conjunction with a particular aspect of the invention are to be understood to be applicable to any other aspect described herein unless incompatible therewith. All of the features disclosed in the specification, and claims, abstract and drawings, and/or all of the steps of any method or process disclosed, can be combined in any combination, except combinations where at least some of such features or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. All publications and references cited herein are expressly incorporated herein by reference in their entirety.

What is claimed is:

1. A sensor and housing assembly 100 for a single-use bioreactor system, comprising a device for operatively associating a sensor with a flexible wall, the device comprising:
   an internal housing portion 130 removable and variably positionable on an internal surface of the flexible wall 112, the internal housing portion 130 comprising:
   an internal portion of a chemical detector sensor sealably embedded in a detector sensor housing 132, and
   at least one portion of an internal magnetic material 136, 138 positioned within the internal housing portion 130 for variably positioning and removing the internal housing portion 130 on the internal surface of the flexible wall 112; and
   an external housing portion 140 positioned on an external surface of a support structure 110 adjacent to the external surface of the flexible wall 114, the external housing portion 140 comprising:
   an external portion of an activator sensor sealably embedded in an activator sensor housing 142; and
   at least one portion of an external magnetic material 146, 148 positioned within the external housing portion 140 or adjacent thereto for holding the detector sensor 132 proximate and aligned to activator sensor 142, and for variably positioning the internal housing portion 130 on the internal surface of the flexible wall 112 by magnetic interaction between the at least one portion of the external magnetic material 146, 148 and the at least one portion of the internal magnetic material 136, 138 within the internal housing portion 130.

2. The sensor and housing assembly of claim 1, wherein the external housing portion 140 is removable and variably positionable on the external surface of the support structure 110.

3. The sensor and housing assembly of claim 1, wherein the external housing portion 140 is positionable on an external surface of a support structure comprising a steel vessel.

4. The sensor and housing assembly of claim 1, wherein at least one of the internal magnetic material and the external magnetic material comprises a ferro-magnetic material.

5. The sensor and housing assembly of claim 1, wherein the sensor is an optical chemical sensor.

6. The optical sensor of claim 5, wherein the sensor is an oxygen sensor.

7. The sensor and housing assembly of claim 1, wherein the sensor is a pH sensor.

8. A sensor and housing assembly 400 for a single-use bioreactor system, comprising a device for operatively associating a sensor with a flexible wall, the device comprising:
   an internal housing portion 430 removable and variably positionable on an internal surface of the flexible wall 412, the internal housing portion 430 comprising:
   an internal portion of a chemical detector sensor sealably embedded in a detector sensor housing 432, and
   at least one portion of an internal magnetic material 436, 438, positioned within the internal housing portion 430 for variably positioning and removing the internal housing portion 430 on the internal surface of the flexible wall 412; and
   an external housing portion 440 positioned on the external surface of the flexible wall 414, the external housing portion 440 comprising:
   an external portion of an activator sensor sealably embedded in an activator sensor housing 442; and
   at least one portion of an external magnetic material 446, 448, positioned within the external housing portion 440 or adjacent thereto for holding the detector sensor 432 proximate and aligned to the activator sensor 442, and for variably positioning the internal housing portion 430 on the internal surface of the flexible wall 412 by magnetic interaction between the at least one portion of the external magnetic material 446, 448, and the at least one portion of the internal magnetic material 436, 438 within the internal housing portion 430.

* * * * *